United States Patent [19]
Munson et al.

[11] Patent Number: 6,057,487
[45] Date of Patent: May 2, 2000

[54] METHOD FOR PRODUCING 2,6-DMN FROM MIXED DIMETHYLNAPHTHALENES BY CRYSTALLIZATION, ADSORPTION AND ISOMERIZATION

[75] Inventors: Curtis L. Munson, Oakland; Patrick C. Bigot; Zunqing Alice He, both of San Rafael, all of Calif.

[73] Assignee: Chevron Chemical Company, San Ramon, Calif.

[21] Appl. No.: 09/000,858

[22] Filed: Dec. 30, 1997

[51] Int. Cl.[7] .............................. C07C 7/14; C07C 7/12; C07C 5/22

[52] U.S. Cl. .............................. 585/814; 585/812; 585/815; 585/828; 585/804; 585/320; 585/322; 585/323; 585/479

[58] Field of Search .............................. 585/320, 322, 585/323, 812, 814, 815, 804, 828, 479, 26, 806

[56] References Cited

U.S. PATENT DOCUMENTS

| | | | |
|---|---|---|---|
| 3,109,036 | 10/1963 | Suld et al. | 260/668 |
| 3,153,675 | 10/1964 | Mason, Jr. | 585/316 |
| 3,153,676 | 10/1964 | Allen et al. | 585/320 |
| 3,235,615 | 2/1966 | Allen et al. | 585/304 |
| 3,244,758 | 4/1966 | Eberhardt | 585/320 |
| 3,249,644 | 5/1966 | Hahn, Jr. | 585/304 |
| 3,336,411 | 8/1967 | Benham | 585/320 |
| 3,485,885 | 12/1969 | Peterkin et al. | 585/813 |
| 3,541,175 | 11/1970 | Hedge | 260/674 |
| 3,594,436 | 7/1971 | Hedge et al. | 260/674 N |
| 3,668,267 | 6/1972 | Hedge | 260/674 SA |
| 3,772,399 | 11/1973 | Hedge | 585/479 |
| 3,775,498 | 11/1973 | Thompson | 585/320 |
| 3,798,280 | 3/1974 | Shimada et al. | 585/479 |
| 3,803,253 | 4/1974 | Suld et al. | 260/668 A |
| 3,839,479 | 10/1974 | Hedge | 260/674 N |
| 3,890,403 | 6/1975 | Shimada et al. | 585/478 |
| 4,014,949 | 3/1977 | Hedge | 585/831 |
| 4,777,312 | 10/1988 | Bakas et al. | 585/481 |
| 4,791,235 | 12/1988 | Maki et al. | 585/806 |
| 4,795,847 | 1/1989 | Weitkamp et al. | 585/467 |
| 4,835,334 | 5/1989 | Hobbs et al. | 585/831 |
| 4,962,260 | 10/1990 | Sikkenga et al. | 585/481 |
| 4,963,248 | 10/1990 | Yano et al. | 208/135 |
| 5,004,853 | 4/1991 | Barger et al. | 585/481 |
| 5,043,501 | 8/1991 | Del Rossi et al. | 585/323 |
| 5,059,742 | 10/1991 | Miyashi et al. | 585/860 |
| 5,064,630 | 11/1991 | Verduijn et al. | 423/328 |
| 5,146,040 | 9/1992 | Verduijn et al. | 585/825 |
| 5,220,098 | 6/1993 | Nakamura et al. | 585/812 |
| 5,254,769 | 10/1993 | Takagawa et al. | 585/477 |
| 5,268,523 | 12/1993 | Fellmann et al. | 585/446 |
| 5,300,721 | 4/1994 | Takeuchi et al. | 585/451 |
| 5,481,055 | 1/1996 | Takagawa et al. | 585/481 |
| 5,495,060 | 2/1996 | Takagawa et al. | 585/481 |
| 5,510,563 | 4/1996 | Smith et al. | 585/812 |
| 5,744,670 | 4/1998 | Motoyuki et al. | 585/320 |

*Primary Examiner*—Walter D. Griffin
*Attorney, Agent, or Firm*—W. B. Haymond; D. M. Tuck

[57] ABSTRACT

A method is disclosed to produce 2,6-dimethylnaphthalene (2,6-DMN), used for the production of polyethylene naphthalate, at high purity and high yield from a mixture of dimethylnaphthalene isomers without limitation to the specific isomers present in the feed by a series of fractionation, crystallization and adsorption steps.

36 Claims, 3 Drawing Sheets

METHOD FOR PRODUCING 2,6-DMN FROM MIXED DIMETHYLNAPHTHALENES BY CRYSTALLIZATION, ADSORPTION AND ISOMERIZATION

FIELD OF THE INVENTION

The invention relates to a process for the separation of 2,6-DMN from other DMN isomers and conversion of non-2,6-DMN isomers into the desired 2,6-DMN product.

BACKGROUND OF THE INVENTION 2,6-DMN is an intermediate produced during the manufacture of 2,6-naphthalene dicarboxylic acid (2,6-NDA) and 2,6-naphthalene dicarboxylate (2,6-NDC). 2,6-NDA and 2,6-NDC are monomers either of which, when combined with ethylene glycol, reacts to make polyethylene naphthalate (PEN), a polyester with unique and advantageous commercial applications in films, fibers, and packaging.

The isomers of dimethylnaphthalene are difficult to separate from one another by distillation because their boiling points are very similar. Technology exists to recover 2,6-DMN by crystallization, or by adsorption, or by adsorption followed by crystallization. It is difficult to separate 2,6-DMN from 2,7-DMN by crystallization alone because they form a eutectic. It is expensive to recover 2,6-DMN from mixed DMNs by adsorption alone because there are no known materials that selectively adsorb 2,6-DMN. In previous technology, when adsorption and crystallization steps were combined, the adsorption step was always used to remove the majority of the undesired DMN isomers.

Furthermore, the adsorption step was often followed by an additional crystallization step to obtain the desired product purity.

An additional complication in the commercial production of 2,6-DMN is the difficulty of converting DMN isomers other than 2,6-DMN into the desired 2,6-DMN isomer. It is well known that during DMN isomerization, it is easy to move methyl groups on a naphthalene ring when they migrate from an alpha position (i.e., 1, 4, 5 or 8) to a beta position (i.e., 2, 3, 6 or 7) or vice versa, but it is difficult when the methyl groups must rearrange from one beta position to another. DMN isomers have been classified into groups called "triads" within which isomerization is readily accomplished. These triads are (1) 1,5-DMN, 1,6-DMN, and 2,6-DMN; (2) 1,7-DMN, 1,8-DMN, and 2,7-DMN; and (3) 1,3-DMN, 1,4-DMN, and 2,3-DMN. The tenth isomer, 1,2-DMN, consists of two methyl groups in adjacent alpha and beta positions and does not fall into one of the aforementioned triads.

Producers have developed methods for making commercial quantities of 2,6-DMN by avoiding co-producing the 2,7-DMN isomer because of the difficulty in recovering 2,6-DMN at high yield in the presence of 2,7-DMN. Furthermore, producers have tried to avoid making isomers outside the 2,6-triad because of the difficulty in isomerizing across triads. Isomers that cannot be converted to 2,6-DMN represent a yield loss and inefficient use of raw materials. Additionally, adsorption is not practical when the concentration of 2,6-DMN in the feed stream is low because there are no known materials that will preferentially adsorb 2,6-DMN over the other isomers. These limitations often necessitate the use of expensive raw materials and controlled organic synthesis reactions that can produce only isomers in the 2,6-triad, such as alkylation of butadiene and ortho-xylene, and methylation of methylnaphthalene.

Technologies relating to the purification of 2,6-DMN from DMN isomer mixtures by crystallization, adsorption and distillation are known as are technologies relating to the isomerization of non-2,6-DMN to 2,6-DMN.

Separation of DMN isomers by crystallization is relatively straightforward if the feed composition is quite high in 2,6-DMN isomer, or if a low yield is acceptable, or if the feed to be crystallized consists of isomers within a triad. If the concentration of 2,6-DMN is well above the eutectic composition, simple crystallization can produce pure 2,6-DMN in high yields. If the concentration of 2,6-DMN is slightly above the eutectic composition, low yield of high purity DMN can be obtained. If the mixture consists of isomers within the 2,6-DMN triad, the unrecovered material, a mixture of 1,5-DMN, 1,6-DMN and 2,6-DMN, can be easily isomerized to produce a mixture with 2,6-DMN above the eutectic composition. Crystallization alone becomes insufficient to purify mixed DMNs to make 2,6-DMN when both the 2,6-DMN and 2,7-DMN isomers are present because they form a eutectic.

The feasibility of adsorption separation for DMN isomers has been demonstrated. However, no material has been published that selectively adsorbs 2,6-DMN from a feed of mixed DMN's. This limitation makes it expensive to recover 2,6-DMN from mixed DMNs by adsorption alone because the adsorption equipment must be very large in order to remove all components other than 2,6-DMN from a feed stream that contains small quantities of 2,6-DMN.

One technique for overcoming the limitations of 2,6-DMN purification by crystallization or by adsorption is to combine the two technologies. Such a combination has always previously been done by using the adsorption step as a feed pretreatment step prior to the crystallization step.

An alternative technique to break the 2,6-DMN/2,7-DMN eutectic is to partially or completely saturate the naphthalene ring. The resulting decalins or tetralins do not form a eutectic at the same composition as the dimethylnaphthalenes, so an incremental quantity of the 2,6- and 2,7-isomers can be recovered by alternately hydrogenating and dehydrogenating the DMN feed.

It has been disclosed that a noneutectic DMN mixture containing 2,6-DMN and 2,7-DMN along with smaller amounts of other hydrocarbons can be sublimated so that the remaining solid is a mixture of 2,6-DMN and 2,7-DMN. However, no teaching is given that sublimation can be used to purify a 2,6-DMN/2,7-DMN mixture which is in the form of an eutectic composition.

Previous isomerization technologies have been limited to intra-triad conversions, i.e., movement of methyl groups between adjacent alpha and beta positions only. Santilli and Chen, U.S. patent application Ser. No. 08/892,508, filed Jul. 14, 1997, now U.S. Pat. No. 6,015,930, which is incorporated herein by reference, discloses a method of isomerizing a feed of any composition of mixed dimethylnaphthalenes having a methyl group on each ring to a product that approximates an equilibrium mixture of mixed dimethylnaphthalenes having a methyl group on each ring (i.e., the 2,6-DMN and 2,7-DMN triads). The method of the present invention incorporates this method of isomerization across the two triads.

Researchers have integrated separation and isomerization technologies in an attempt to improve the overall process of 2,6-DMN production. These various attempts to integrate the technologies have had limited success because the various steps of the process suffer from such problems as low yields or the inability to isomerize between triads.

The technologies discussed above relate either generally or specifically to certain aspects of the presently claimed
} invention. These technologies are either not very effective or not economical for obtaining substantially pure 2,6-DMN from feeds containing a variety of DMN isomers outside the 2,6-triad. What is needed is an economic method to produce 2,6-DMN at high purity and high yield from a mixture of DMN isomers without being limited to the specific isomers present in the feed. A new method should convert isomers other than 2,6-DMN into the desired 2,6-DMN isomer in order to have an acceptable yield of 2,6-DMN from the feed source. The present invention accomplishes these goals.

SUMMARY OF THE INVENTION

One object of the present invention is to provide an economical method of separating 2,6-DMN from a mixture of DMN isomers in relatively high and stable yields. The method is highly efficient in its use of dimethylnaphthalene isomers, thereby enhancing the industrial significance of the process.

Another object of the present invention is to provide a method of purifying 2,6-DMN from a feed mixture of dimethylnaphthalene isomers and near-boiling compounds comprising the steps of crystallizing the mixture to precipitate a eutectic composition comprising 2,6-dimethylnaphthalene and 2,7-dimethylnaphthalene; optionally dissolving the eutectic composition in a solvent; and recovering a predominantly 2,6-dimethylnaphthalene composition from the dissolved eutectic composition by adsorbing out non-2,6-dimethylnaphthalenes onto an adsorption column. The crystallization accomplishes high recovery of 2,6-DMN independent of isomers present, while the adsorption step accomplishes high purity of 2,6-DMN independent of isomers present.

Still another object of the invention is to fractionate the feed mixture of dimethylnaphthalene isomers and near-boiling compounds before it is purified by crystallization and adsorption to remove compounds that are either more volatile or less volatile than 2,6-DMN and 2,7-DMN. The fractionation step simplifies downstream purification and reduces the size of downstream equipment.

Yet another object of the invention is to recycle the DMN isomers, predominantly isomers other than 2,6-DMN, that are either retained in the mother liquor during the crystallization step or recovered in the extract stream during the adsorption step to be isomerized into a mixture that closely approximates an equilibrium distribution of dimethylnaphthalene isomers, that can then be recycled back to the fractionation step. Hydroisomerization/dehydrogenation is a highly efficient, nearly equilibrium conversion of isomers other than 2,6-DMN into the desired 2,6-isomer.

DETAILED DESCRIPTION OF THE INVENTION

Figure 1:
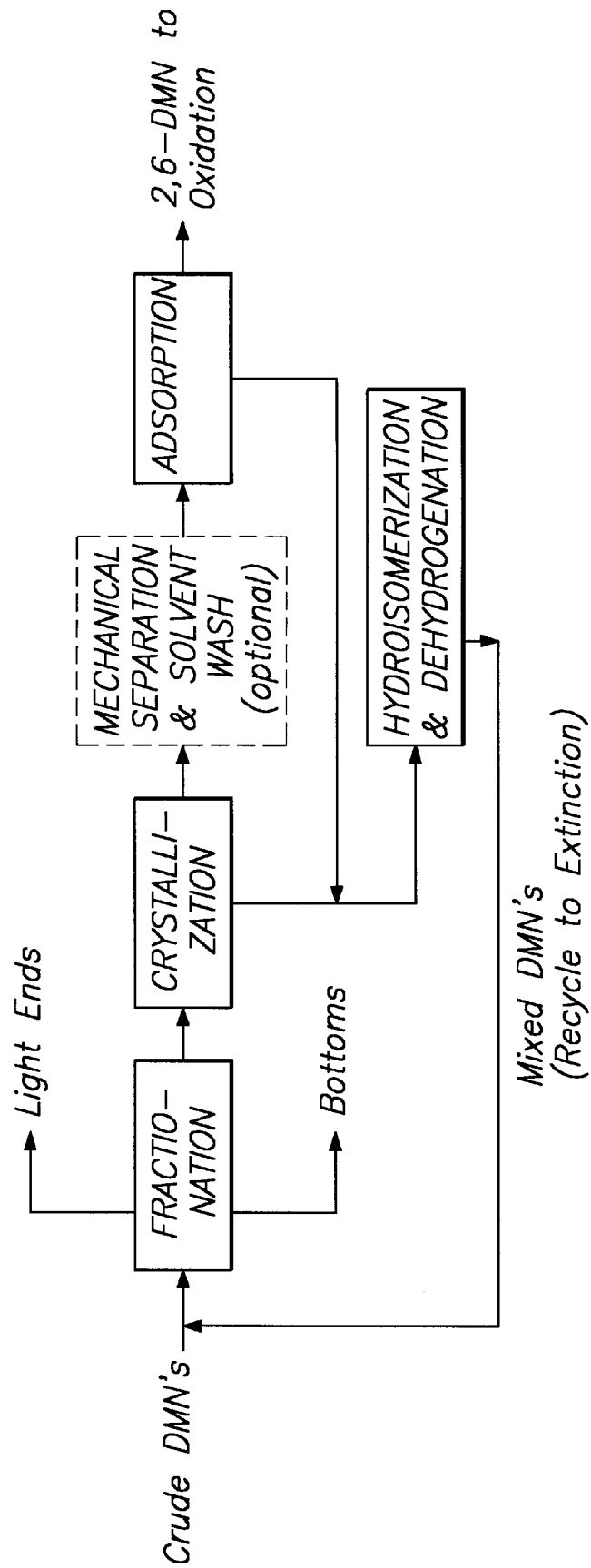
FIG. 1 is a simplified process flow drawing of a preferred embodiment of the invention.

A continuous process for the recovery and purification of 2,6-DMN from a hydrocarbon feedstock containing mixed dimethylnaphthalene isomers has been developed. The process of this invention is comprised of fractionation, crystallization, adsorption, and isomerization steps. A simplified process flow drawing of a preferred embodiment of this process is shown in FIG. 1.

The feed for the new process is a hydrocarbon mixture that contains isomers of dimethylnaphthalene (DMN). The concentration of DMNs in the feed is preferably greater than 5 wt. %, more preferably greater than 50 wt. %, and most preferably greater than 80 wt. %. Potential sources of hydrocarbon feed are petroleum refinery streams, coal tar liquids, or the reaction products of a synthetic chemical processing route. Examples of petroleum refinery streams include, but are not limited to, higher boiling aromatic fractions produced in reforming of petroleum naphtha to produce high octane gasoline; aromatic fractions produced by the thermal cracking of catalytically reformed gasoline; aromatic fractions produced by the catalytic cracking of thermally reformed naphtha; aromatic concentrates obtained from catalytic gas oil produced in catalytic cracking or petroleum; and crude unit gas oils. The mixed DMNs could be produced from a chemical synthesis route such as, but not limited to, dehydrocyclization of pentyltoluene made from the alkylation of pentenes and toluene, dehydrocyclization of pentenyltoluene made from the alkenylation of ortho-xylene and butadiene, or methylation of methylnaphthalene. In a preferred embodiment, fresh feed is commingled with recycle streams from the downstream isomerization step of this process. Alternatively, the recycle can be introduced downstream of the fractionation unit.

In a preferred embodiment, the feed is fractionated to obtain a heart cut that is rich in DMN isomers and boils in the approximate range of 480–520° F., preferably in the range 500–510° F. Fractionation can be accomplished by conventional distillation in one or more distillation columns. If one column is used, multiple feed and draw streams are required. The preferred configuration is to use two columns. In the first column, components more volatile than 2,6-DMN are distilled overhead and can be recovered as valuable byproducts, recycled to earlier steps of the DMN production process, or used as fuel. In the second column, components less volatile than 2,6-DMN are collected from the bottoms and can be recovered as valuable by-products, recycled to earlier steps of the DMN production process, or used as fuel. Fractionation may not be required prior to crystallization if the feed has a sufficiently high concentration of DMN.

The fractionated DMNs can contain near-boiling components such as, but not limited to, pentyltoluenes, pentenyltoluenes, methylnaphthalenes, ethylnaphthalenes, dimethylhydronaphthalenes, dimethyltetralins, dimethyldecalins, trimethylindans, trimethylnaphthalenes as well as other close-boiling aromatic, paraffinic, and naphthenic compounds. It is desirable to minimize the concentration of components that would crystallize at a temperature above the 2,6-DMN crystallization temperature in order to minimize the simultaneous recovery of impurities with the desired 2,6-DMN product.

In a preferred embodiment, the fractionated DMN mixture is cooled to precipitate 2,6-DMN and a eutectic composition of 2,6-DMN and 2,7-DMN. The final cooling temperature is dependent on the feed composition and whether a solvent is added. For melt crystallization, the final cooling temperature is as high as 230° F. for a feed highly concentrated in 2,6-DMN, or as low as 3° F. for a feed dilute in 2,6-DMN. For the concentration range of interest, the final cooling temperature is in the range of 155° F. to 80° F. For solvent crystallization, the final cooling temperature may vary over a wide range depending on solvent and feed concentration but may range from 230° F. to −120° F., preferably 80° F. to 40° F. Pressure can be from 0 to 3000 psi. An alternative to cooling is to precipitate the 2,6-DMN and a eutectic by a combination of cooling plus pressurizing the system to over 7000–20,000 psi. Crystallization may also be induced by removing solvent by evaporation or by adding agents that reduce the solubility of DMN in solution.

The crystallization may be carried out batchwise or continuously. It may be carried out in one vessel or more than one physically distinct vessel in series. The preferred configuration depends on the relative concentrations of 2,6-DMN and other compounds that would co-precipitate, especially 2,7-DMN. If crystallization is carried out in one vessel, the maximum recovery of 2,6-DMN is achieved by cooling the fractionated DMN mixture to the 2,6-DMN/2,7-DMN eutectic composition until all 2,6-DMN has precipitated. If multiple crystallizers are used in series, 2,6-DMN is partially precipitated from the mother liquor in the first crystallizer, separated from the supernatant, and the supernatant is then transferred to one or more downstream vessels for additional recovery of 2,6-DMN. Throughout the process, 2,6-DMN and the 2,6-DMN/2,7-DMN eutectic crystals are collected together. In the event that isomers other than 2,6-DMN do not co-precipitate in one of the crystallizers and there is a sufficiently high concentration of 2,6-DMN that is greater than the eutectic composition, it may be advantageous to collect and recover essentially pure 2,6-DMN prior to reaching the eutectic point.

The simplest crystallization technique is melt crystallization provided the composition of 2,6-DMN plus 2,7-DMN in the feed mixture of DMNs is at least 20 wt. %, preferably at least 50 wt. %, and more preferably at least 90 wt. %. Melt crystallization can be carried out in either a static or a dynamic design. The mixture of DMN isomers is introduced into the crystallizer and the contents are cooled with a non-contact heat transfer medium. The desired crystals form on and adhere to the heat transfer surface. When essentially all of the 2,6-DMN has solidified, the cooling is halted and the remaining liquid contents are drained from the crystallizer. The heat transfer medium is then heated slightly to melt the solids off of the heat transfer surface. The initial melt will contain a higher concentration of impurities than the bulk of the product so it can be collected separately and routed with the other DMN isomers to the hydroisomerization/dehydrogenation unit in order to increase the purity of the 2,6-DMN/2,7-DMN solution going to the adsorption step. The mixture of liquid 2,6-DMN and 2,7-DMN are sent directly to the adsorption step.

As an alternative, solvent crystallization can be used to separate the 2,6-DMN/2,7-DMN eutectic, and would be the preferred crystallization method for feeds with low concentrations of 2,6-DMN plus 2,7-DMN. A solvent such as a low boiling hydrocarbon like toluene, xylene, octane, or heptane, or an alcohol like methanol, ethanol, or isopropanol, or other classes of solvents such as ethers, or a low molecular weight carboxylic acid like acetic acid, or a combination of solvents could be used. Light aromatic hydrocarbons are preferred solvents with toluene and meta-xylene the most preferred. Non-solvents may be added to enhance precipitation but these may impact final product purity if they cannot be adequately separated in the adsorption step. In a solvent crystallization process, the crystals of 2,6-DMN and 2,7-DMN are mechanically separated from the solution using, for example, filters or centrifuges, and either melted or re-dissolved prior to being sent to the adsorption step. The supernatant mixture will contain all DMN isomers, including trace quantities of 2,6-DMN as well as near-boiling compounds, and is sent to the hydroisomerization/dehydrogenation unit for further processing.

The crystals produced in a solvent crystallization process are optionally washed with another agent such as methanol to remove mother liquor retained between particles and contaminants that may adhere to the surface of the particles. The crystals are once again mechanically separated from the wash solution using, for example, filters or centrifuges. The washing agent is cooled to near the crystallization temperature to minimize DMN dissolving into the wash solvent. Following the wash, the crystals may optionally be dried over mild heat to remove remaining wash agent and to partially sublime DMN isomers other than 2,6-DMN. An acceptable alternative to solvent washing is to partially melt the DMN crystals to remove the liquid impurities as is done in a wash column.

The final purification step is adsorption separation of 2,7-DMN from 2,6-DMN. The adsorption may be performed by either a simple swing-bed unit or, more preferably, a simulated countercurrent moving bed unit. For a swing-bed unit, one bed operates in adsorption mode while another operates in regeneration mode. The adsorbent material selectively adsorbs 2,7-DMN from the feed stream, leaving essentially pure 2,6-DMN in the effluent. When unacceptable amounts of 2,7-DMN appear in the effluent, the operating bed is considered to have reached the useful limit of its capacity to remove 2,7-DMN and it is taken out of service. The other bed is placed on-line while the first bed is regenerated and the cycle repeats itself. Multiple beds can be staggered in adsorption mode and regeneration mode to optimize capital and operating costs. Adsorption and regeneration can be carried out batchwise or continuously. For a simulated countercurrent moving bed unit, the 2,6-DMN/2,7-DMN feed and a suitable desorbent are introduced to the fixed-bed adsorption column at two different locations. Two product streams are drawn from different locations along the column: an extract that contains desorbent with 2,7-DMN and other impurities that were present in the feed, and a raffinate that contains desorbent and essentially pure 2,6-DMN. The DMNs are recovered from their respective adsorber effluent streams via distillation. Desorbent is returned to the adsorber, 2,7-DMN is combined with the supernatant from the crystallizer and routed to the hydroisomerization/dehydrogenation unit, and 2,6-DMN is collected as desired product.

Suitable adsorbents include crystalline aluminosilicates, L-zeolites, X-zeolites, Y-zeolites, Y Offreitite, and Ambersorb® 563 (a carbonaceous adsorbent). The preferred adsorbents are Y-zeolites exchanged with Group I and/or Group II metals (i.e., Na, K, Ca, Ba, etc.) with the most preferred Group I metal being potassium. Suitable desorbents include, but are not limited to, light aromatic hydrocarbons such as toluene, para-xylene, ethylbenzene, and para-diethylbenzene. The preferred desorbents are aromatic hydrocarbons and the most preferred is para-xylene. The desorbent may be a compound with a higher boiling point than dimethylnaphthalene.

The preferred operating conditions for the adsorption process require dissolution of the DMN feed mixture in a solvent. The DMN may be dissolved to any concentration but the preferred concentration range is from 5% to 60% DMN. The solvent may be any liquid that can dissolve DMN and at the same time enhance adsorption selectivity. Suitable solvents are light aromatic hydrocarbons, or aliphatic hydrocarbons with carbon number from 5 to 20, with octane or heptane being the preferred solvents. Operating temperatures can range from 80° F. to 220° F., depending on concentration with a preferred temperature of 140° F. to 180° F. Operating pressure may vary but is set high enough to maintain the solvent and DMN feed in a liquid state through the column. The flow rate may vary but the preferred condition is with a liquid hourly space velocity (LHSV) from 0.1 to 10 hr$^{-1}$.

The adsorbent should be carefully dried to the proper water content to maximize the separation factor between 2,6-DMN and 2,7-DMN. Y-zeolite is a low silica zeolite and, as such, it readily adsorbs moisture from air. If the water content on the adsorbent is too high, the adsorbed water will reduce the accessibility of the adsorbate molecules to the high surface area of the zeolite. However, if the water content is too low, the adsorption selectivity of 2,6-DMN and 2,7-DMN decreases.

Feed to the two-step hydroisomerization/dehydrogenation unit consists of mixed DMNs depleted of 2,6-DMN as well as near-boiling components. In a preferred embodiment, the source of these DMNs is the crystallizer supernatant and adsorber extract as previously described. In addition, any feed that is substantially depleted in 2,6-DMN, such as petroleum refinery streams, coal tar liquids, or the reaction products of a synthetic chemical processing route can be used exclusively or as co-feed with the supernatant and extract.

Hydroisomerization/dehydrogenation is carried out as described in U.S. patent application Ser. No. 08/892,508 (Santilli and Chen), filed Jul. 14, 1997, now U.S. Pat. No. 6,015,930, which is incorporated herein by reference. The aromatic rings of the DMN molecules in the feed are first partially or completely saturated to form dimethyltetralins (DMTs) and dimethyldecalins (DMDs) over a dual-functional metal-acid catalyst (e.g., sulfided PdS/Boron-Beta with Al, sulfided PtS/Boron-Beta with Al, sulfided PdS/Y-zeolite, or non-sulfided Pd/Boron-Beta with Al). Methyl group migration readily occurs at reaction conditions to produce a distribution of DMTs and DMDs with one methyl group on each ring. The isomerized structures are converted back to an essentially equilibrium distribution of DMNs by passing over a second catalyst in a subsequent dehydrogenation reactor. The second catalyst is a reforming catalyst that suppresses transalkylation, dealkylation, and cracking reactions (e.g., sulfided Pt/Re/Al$_2$O$_3$, sulfided Pt/Na-ZSM-5, or PtS/Cs/Boron-SSZ-42). In a preferred embodiment, the yield of partially saturated species (DMT) from the hydroisomerization reaction should be at least 5 weight percent. In a more preferred embodiment, the yield of partially saturated species (DMT) should be at least 10 weight percent. The weight hourly space velocity (WHSV) can vary from about 0.1 to 100 hr$^{-1}$, the pressure can vary from 0 to 3000 psi, the hydrogen/hydrocarbon molar ratio can vary from <0.1 to 100, and the reactor temperature can vary from about 300° F. to 1000° F. Approximately 50% conversion of 2,7- to 2,6-triad dimethylnaphthalenes with little or no formation of methylnaphthalenes, 1,2-DMN, 1,3-DMN, 1,4-DMN, 2,3-DMN or trimethylnaphthalenes can be achieved with this two-step process through optimization of the process conditions. In all the embodiments of the hydroisomerization/dehydrogenation process, the dimethylnaphthalene feed can be flowed over the catalyst along with hydrogen gas or the reaction can be performed batch-wise.

DMN produced in the hydroisomerization/dehydrogenation unit is recycled and recovered as product and DMN isomers other than 2,6-DMN are recycled to extinction. In a preferred embodiment, the mixed-DMN product from the hydroisomerization/dehydrogenation unit, hereinafter referred to as isomerate, is recycled and combined with the hydrocarbon fresh feed to the fractionation unit for removal of light and heavy contaminants. Alternatively, contaminants in the isomerate could be removed in a separate and distinct distillation unit and recovered as byproducts or fuel. For example, MN and TMN could be transalkylated to produce DMN and increase the overall yield of this process. In still another embodiment, in the absence of light or heavy contaminants, the isomerate can be commingled with distilled DMNs from the fractionation column as feed to the crystallization unit.

EXAMPLES

Example 1

The following example illustrates that a complex mixture of DMN isomers can be separated by dissolving them in a solvent and passing the solution through an adsorbent column. Furthermore, this example also illustrates that 2,6-DMN and 2,7-DMN isomers are well separated from each other in this way. This example also illustrates that other isomers, such as 1,6-DMN, 1,5-DMN and 1,7-DMN, elute before 2,7-DMN and close to 2,6-DMN. Therefore, using an adsorption purification process to recover 2,6-DMN when the feed contains 1,6-DMN, 1,5-DMN and 1,7-DMN isomers, as in prior art, has a reduced efficiency and therefor is more expensive to operate. The adsorption process becomes much more efficient when a prior step is used to remove or reduce the quantity of isomers other than 2,6-DMN and 2,7-DMN.

Figure 2:
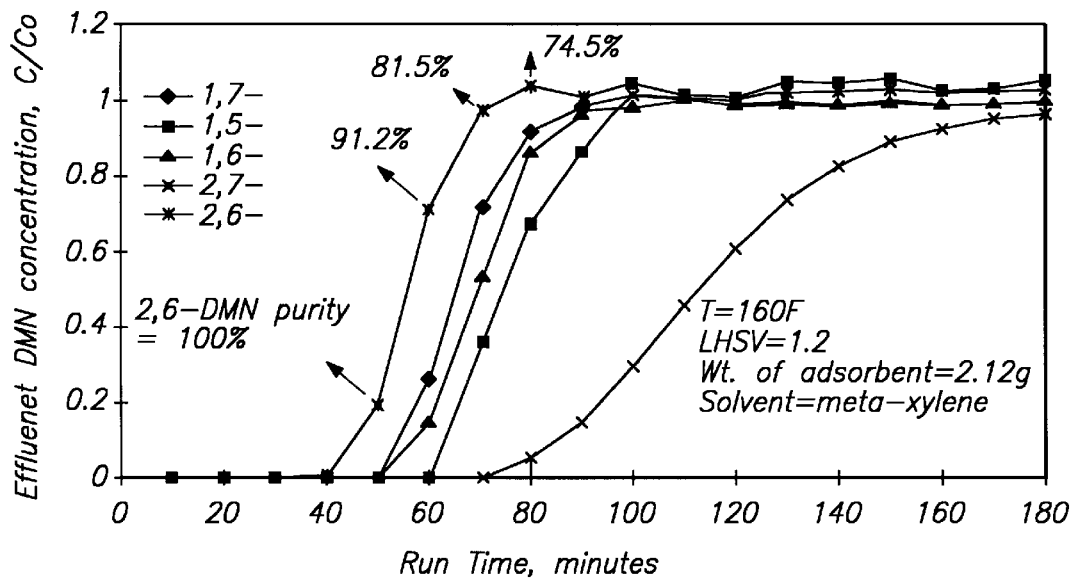
FIG. 2 is a graphical representation of the amounts of various DMN isomers in an effluent over time.

A mixture of DMN isomers having the composition 8.93% 1,7-DMN; 1.88% 1,5-DMN; 8.94% 1,6-DMN; 31.05% 2,7-DMN; and 49.20% 2,6-DMN was dissolved in meta-xylene and passed through a column of potassium-exchanged Y (K-Y) zeolite adsorbent. The weight of the adsorbent was 2.12 grams and the liquid hourly space velocity (LHSV) of the column was 1.2 hr$^{-1}$. At the interval between 40 and 50 minutes run time, the DMN in the effluent was approximately 100% 2,6-DMN; and at 50 minutes run time the proportion of concentration of effluent to concentration of feed, $C_{eff}/C_o$, was approximately 0.2. At the interval between 50 and 60 minutes, the DMN in the effluent was approximately 91.2% 2,6-DMN; and at 60 minutes run time, the $C_{eff}/C_o$ was approximately 0.75. At the interval between 60 and 70 minutes, the DMN in the effluent was approximately 81.5% 2,6-DMN; and at 70 minutes run time, the $C_{eff}/C_o$ was approximately 0.975. At the interval between 70 and 80 minutes, the DMN in the effluent was approximately 74.5% 2,6-DMN, and at 80 minutes run time, the $C_{eff}/C_o$ was approximately 1.05. A more complete graphical representation of the amounts of the various DMN isomers in the effluent over time is shown in FIG. 2.

Example 2

The following example illustrates the use of a coarse crystallization step to reduce the level of non-2,6/2,7-isomers.

A mixture of isomers of 6.3 grams 1,6-DMN, 5,7 grams 1,7-DMN, 1.8 grams 1,5-DMN, 6.3 grams 2,7-DMN, and 6.3 grams 2,6-DMN was dissolved in 15 grams toluene, then cooled in a stirred vessel to 32° F. The solution was filtered and a precipitate recovered. The precipitate was rinsed with cold methanol, and then dried at ambient temperature under vacuum overnight. The product was found to be 90% 2,6-DMN, 6% 2,7-DMN, and 3% other DMN isomers.

Example 3

This example illustrates the overall separation process to produce pure 2,6-DMN from a feed of reformate oil. Reformate oil from a chemical synthesis was purified to produce pure 2,6-DMN. The reformate had the composition shown below in Table A:

TABLE A

| Component | Weight Percent |
|---|---|
| light components | 0.06 |
| toluene | 1.8 |
| $C_2$ alkylbenzenes | 0.60 |
| $C_3$ alkylbenzenes | 1.88 |
| $C_4$ alkylbenzenes | 2.61 |
| indan | 0.17 |
| $C_5$ alkylbenzenes | 2.92 |
| $C_2$ indans | 0.86 |
| naphthalene | 4.28 |
| $C_6$ alkylbenzenes | 41.04 |
| $C_3$ indans | 11.83 |
| $C_3$ indenes | 0.91 |
| methylnaphthalenes | 6.85 |
| dimethylnaphthalenes | 14.7 |
| other | 9.49 |

The first purification step was to distill a heart cut between 500° F. and 520° F. The resulting distillate composition is given below in Table B.

Figure 3:
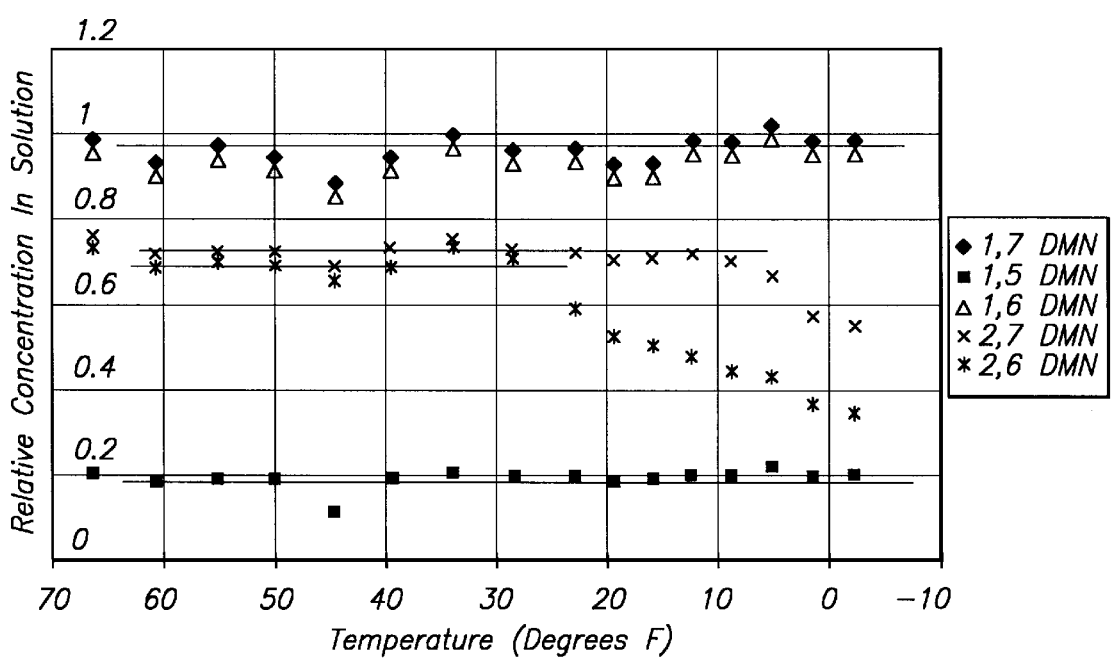
FIG. 3 is a graphical representation of a solvent crystallization experiment.

38 grams of distillate was diluted with 38 grams of toluene and cooled from 80° F. to −5° F. at a rate of 0.3° F./min in a stirred batch crystallizer. The relative concentration of various DMN isomers in solution during this process is shown in FIG. 3. In FIG. 2, it can be seen that the concentration of 2,6-DMN was reduced as temperature was reduced below 30° F. At temperatures below 5° F., 2,7-DMN concentration also drops. However, the other isomers present remained substantially in solution. These isomers were therefore phase separated from the 2,6-DMN and 2,7-DMN. The solid precipitate formed was collected and separated from the adhering bulk fluid. The resulting precipitate composition is given below in Table B.

The precipitate was dissolved in m-xylene and fed to a column of adsorbent with K-Y zeolite. Effluent was recovered and dried. Product was essentially pure 2,6-DMN.

TABLE B

| Compound | Distillate (wt %) | Precipitate (wt %) | Product (wt %) |
|---|---|---|---|
| 1,7-dimethylnaphthalene | 26.0 | 5.3 | |
| 1,3-dimethylnaphthalene | 0.7 | 0 | |
| 1,5-dimethylnaphthalene | 5.5 | 0 | |
| 1,6-dimethylnaphthalene | 25.9 | 5.4 | |
| 2,7-dimethylnaphthalene | 19.8 | 13.1 | |
| 2,6-dimethylnaphthalene | 18.9 | 76.2 | >99.9 |
| Other | 3.2 | | |

Example 4

This example illustrates the use of rough crystallization followed by adsorption where the feed has a high proportion of 2,6-DMN.

83.5 grams of a mixture of DMNs and meta-xylene (with the composition shown in Table C) was charged into a 250 ml glass-jacketed agitation vessel. A coolant was passed through the jacket to cool the solution from 75° F. to 45° F. at the rate of 1.8° F. every 7 minutes. Solids precipitated and the resulting crystals were filtered th rough an 8 micron filter paper and recovered. The crystals were washed with a small amount of methanol and dried under vacuum. The purified crystals weighed 1.25 grams and the composition of the solids analyzed is shown in Table C. The recovery of 2,6-DMN in this crystallization example was calculated to be 16.4%.

TABLE C

| Component | M-xylene | 2,6-DMN | 2,7-DMN | 1,6-DMN | 1,7-DMN | 1,5-DMN |
|---|---|---|---|---|---|---|
| Feed: % | 81.27 | 8.79 | 3.17 | 2.55 | 2.73 | 0.62 |
| Crystal (solvent free) | | 98.85 | 1.15 | | | |

Figure 4:
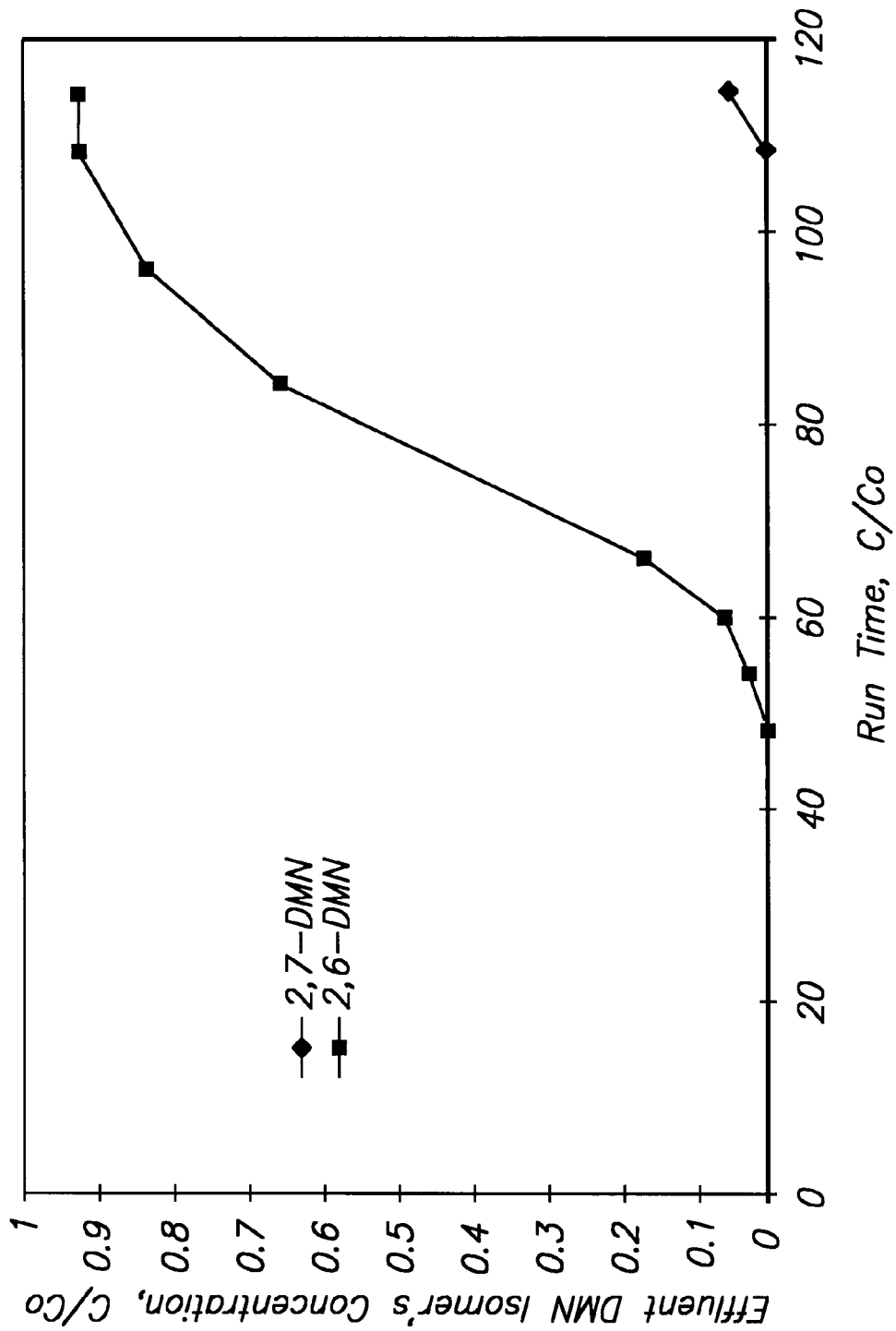
FIG. 4 is a graphical representation of the amounts of 2,6-DMN versus 2,7-DMN in an effluent over time.

The recovered crystals were dissolved in meta-xylene to give a solution of 5% DMN. The above solution was pumped through a stainless steel column (width ⅜"; length 12") packed with 5.7 grams of powdered K-Y zeolite. The effluent concentration of DMN isomers was measured over time and is shown in FIG. 4. Solution was recovered for 105 minutes at which time 2,6-DMN breakthrough was detected. The effluent recovered was dried and the product was pure 2,6-DMN.

Example 5

This example illustrates the additional purification that can be obtained by a partial sublimation process that occurs while drying.

A sample 2,6-DMN containing other DMN isomers was rinsed with cold methanol. The methanol-wet mixture was analyzed and found to have the composition reported, on a solvent-free basis, in Table D. The moist solid was dried at room temperature overnight under vacuum. The resulting composition is also reported in Table D.

TABLE D

| | Wet Sample Composition (solvent-free basis) | Dried Sample Composition |
|---|---|---|
| 2,6-DMN | 52.3% | 87.8% |
| 2,7-DMN | 13.6% | 5.8% |
| 1,6-DMN | 11.1% | 2.0% |
| 1,5-DMN | 6.1% | 0.9% |
| 1,7-DMN | 13.9% | 2.5% |
| other | 3.0% | 1.0% |

Example 6

This example illustrates the additional purification that can be obtained by a partial sublimation process that occurs during a drying step.

A sample 2,6-DMN containing 2,7-DMN isomers was rinsed with cold acetone. The acetone-wet mixture was analyzed and found to have the composition reported, on a solvent-free basis, in Table E. The moist solid was dried at room temperature overnight under vacuum. The resulting composition is also reported in Table E.

TABLE E

| | Wet Sample Composition (solvent-free basis) | Dried Sample Composition |
|---|---|---|
| 2,6-DMN | 91.7% | >99.9% |
| 2,7-DMN | 8.3% | <0.1 |

Although a few embodiments of the invention have been described in detail above, it will be appreciated by those skilled in the art that various modifications and alterations can be made to the particular embodiments shown without materially departing from the novel teachings and advantages of the invention. Accordingly, it is to be understood that all such modifications and alterations are included within the spirit and scope of the invention as defined by the following claims.

Footnote: Ambersorb® is a registered trademark of Rohm & Haas Company.

What is claimed is:

1. A method of purifying 2,6-dimethylnaphthalene from a feed mixture of dimethylnaphthalene isomers and near-boiling compounds comprising the steps of:
   (a) crystallizing the mixture to precipitate out of a supernatant a precipitate comprising 2,6-dimethylnaphthalene and 2,7-dimethylnaphthalene;
   (b) dissolving the precipitate in a solvent; and
   (c) passing the dissolved precipitate through an adsorbent to recover an effluent comprising 2,6-dimethylnaphthalene.

2. The method according to claim 1, wherein the method further comprises, before step (a), a fractionating step to remove compounds more volatile and less volatile than 2,6-dimethylnaphthalene and 2,7-dimethylnaphthalene.

3. The method according to claim 2, further comprising isomerizing dimethylnaphthalene isomers other than 2,6-dimethylnaphthalene that are retained in the supernatant from step (a) or adsorbed onto the adsorbent from step (c) to convert the isomers to a mixture consisting essentially of an equilibrium mixture of dimethylnaphthalene isomers.

4. The method according to claim 3, wherein the equilibrium mixture of dimethylnaphthalene isomers is recycled back to the fractionating step.

5. The method according to claim 3, wherein the equilibrium mixture of dimethylnaphthalene isomers is recycled back to the crystallizing step.

6. The method according to claim 2, wherein, after step (c), the method further comprises purifying the effluent by a method comprising:
   (a) cooling the effluent to produce solid precipitate;
   (b) washing the solid precipitate; and
   (c) drying the washed precipitate under conditions permitting partial sublimation of isomers other than 2,6-dimethylnaphthalene from the precipitate.

7. The method of claim 1, wherein the feed mixture is prepared by a process comprising the steps of:
   (a) alkylation of toluene with a $C_5$ olefin or mixed $C_5$ olefins in the presence of an alkali metal to form pentyltoluenes; and
   (b) dehydrocyclization of the pentyltoluenes over a catalyst comprising a Group VIII metal or a mixture of Group VIII metals and a support material.

8. The method of claim 7, wherein the Group VIII metal is selected from the group consisting of Pt, Pd, Ni and Ir.

9. The method of claim 7, wherein the support material is alumina.

10. The method of claim 7, wherein the catalyst further comprises a metal selected from the group consisting of Re, Ge and Sn.

11. The method of claim 1, wherein the feed mixture is prepared by a method comprising the steps of:
   (a) alkenylation of ortho-xylene with butadiene to form pentenyltoluenes; and
   (b) dehydrocyclization of the pentenyltoluenes in one or more steps to form a mixture of dimethylnaphthalene isomers.

12. The method of claim 1, wherein the feed mixture is prepared by a process comprising alkylating methylnaphthalene to form mixed dimethylnaphthalenes.

13. The method of claim 1, wherein the feed mixture is prepared by a process comprising fractionation of mixed hydrocarbon streams resulting from petroleum refining.

14. The method of claim 1, wherein the feed mixture is prepared by a process comprising fractionation of mixed hydrocarbon streams found in coal tar liquids.

15. The method of claim 1, wherein, in step (a), the mixture is cooled.

16. The method of claim 1, wherein, in step (a), the mixture is cooled in a solvent.

17. The method of claim 1, wherein, in step (a), the mixture is added to a solvent and the solvent is evaporated.

18. The method of claim 1, wherein step (a) is carried out in one vessel.

19. The method of claim 1, wherein step (a) is carried out by partially precipitating the 2,6-DMN and 2,7-DMN from the supernatant in a first vessel and then by transferring the supernatant to a second vessel to further precipitate 2,6-DMN and 2,7-DMN from the supernatant.

20. The method of claim 1, further comprising, before step (a), cooling the feed mixture to just above 2,6-DMN/2,7-DMN's eutectic point and recovering pure 2,6-DMN.

21. The method of claim 1, wherein step (c) uses two or more adsorption vessels operating as a simulated counter-current moving bed unit.

22. The method of claim 1, wherein step (c) uses two or more adsorption vessels operating as a swing-bed unit.

23. The method of claim 1, wherein the adsorbent comprises a material selected from the group consisting of crystalline aluminosilicates, L-zeolites, X-zeolites, Y-zeolites, Y Offretite, carbonaceous adsorbents and mixtures thereof.

24. The method of claim 23, wherein the adsorbent is exchanged with metals selected from the group consisting of Group I metals, Group II metals and mixtures thereof.

25. The method of claim 24, wherein the adsorbent is exchanged with a Group I metal.

26. The method of claim 25, wherein the adsorbent is exchanged with potassium.

27. The method of claim 1, wherein the solvent in step (b) is a light aromatic hydrocarbon.

28. The method of claim 1, wherein the solvent in step (b) is an aliphatic hydrocarbon having a carbon number from 5 to 20.

29. The method of claim 28, wherein the solvent is heptane.

30. The method of claim 28, wherein the solvent is octane.

31. The method of claim 1, wherein the method further comprises regenerating the adsorbent of step (c) with a desorbent comprised of an organic solvent.

32. The method of claim 31, wherein the organic solvent is a light aromatic hydrocarbon selected from the group consisting of toluene, xylenes, ethylbenzene, and para-diethylbenzene.

33. The method of claim 32, wherein the organic solvent is para-xylene.

34. The method of claim 1, wherein the method further comprises, after step (c), the steps of:
   (a) hydroisomerizing over an acid catalyst the dimethylnaphthalene isomers other than 2,6-dimethylnaphthalene that are retained in the supernatant from step (a) or adsorbed onto the adsorbent in step (c) to produce a mixture of dimethyldecalins and dimethyltetralins; and
   (b) dehydrogenating the mixture of dimethyldecalins and dimethyltetralins.

35. The method of claim 1, wherein the steps are practiced in a continuous manner.

36. The method of claim 1, wherein the steps are practiced in a batch manner.

* * * * *